(12) United States Patent
Nichols et al.

(10) Patent No.: US 10,335,338 B2
(45) Date of Patent: Jul. 2, 2019

(54) APPARATUS FOR APPLYING MULTI-DIMENSIONAL TRACTION TO THE SPINAL COLUMN

(71) Applicant: Nichols Therapy Systems, LLC, Sabetha, KS (US)

(72) Inventors: Jarrod L. Nichols, Manhattan, KS (US); Galen R. Ackerman, Sabetha, KS (US)

(73) Assignee: Nichols Therapy Systems LLC, Manhattan, KS (US)

( * ) Notice: Subject to any disclaimer, the term of this patent is extended or adjusted under 35 U.S.C. 154(b) by 298 days.

(21) Appl. No.: 14/588,809

(22) Filed: Jan. 2, 2015

(65) Prior Publication Data

US 2016/0193098 A1  Jul. 7, 2016

(51) Int. Cl.
*A61G 13/00* (2006.01)
*A61F 5/042* (2006.01)
(Continued)

(52) U.S. Cl.
CPC ............ *A61G 13/009* (2013.01); *A61F 5/042* (2013.01); *A61G 13/08* (2013.01); *A61G 13/121* (2013.01);
(Continued)

(58) Field of Classification Search
CPC .. A61G 13/009; A61G 13/121; A61G 13/122; A61G 13/123; A61G 13/1295;
(Continued)

(56) References Cited

U.S. PATENT DOCUMENTS 2,630,800 A * 3/1953 Voss .................... A61H 1/0222
5/610
2,835,247 A   5/1958 Stabholc
(Continued)

FOREIGN PATENT DOCUMENTS

WO  WO 87/00424     1/1987
WO  WO 2005067860 A1 * 7/2005  ............ A61H 1/005
(Continued)

OTHER PUBLICATIONS

Three Chiropractic Approaches to Scoliosis Correction by Allen Chamberlain—A senior project submitted in partial requirement for the degree of Doctor of Chiropractic—Advisor Dr. Marcus De Geer, D.C., M.D.
(Continued)

*Primary Examiner* — Alireza Nia
*Assistant Examiner* — Adam Baker
(74) *Attorney, Agent, or Firm* — Daniel J. Coughlin; Coughlin Law Office LLC (57) ABSTRACT

A physical medicine table for treating a patient's spine that is capable of providing precise, repeatable, and effective traction force treatment to a patient in multiple dimensions to adjust an unhealthy spinal structure towards a normal, healthy structure. Generally, the spinal structure treatment can be applied to a patient using the described traction device to secure the patient to the adjustable support portions and selectively impart a combination of longitudinal Y-axis traction forces, lateral X-axis traction forces and/or sagittal Z-axis traction forces to the patient using a control system in accordance with a prescribed treatment regimen.

10 Claims, 8 Drawing Sheets

(51) Int. Cl.
*A61G 13/08* (2006.01)
*A61G 13/12* (2006.01)

(52) U.S. Cl.
CPC ......... *A61G 13/122* (2013.01); *A61G 13/123* (2013.01); *A61G 13/1295* (2013.01)

(58) Field of Classification Search
CPC .... A61G 13/1225; A61G 7/015; A61G 7/008; A61G 7/005; A61G 7/012; A61G 7/018; A61G 7/08; A61G 7/065; A61G 7/002; A61G 7/05; A61G 7/0508; A61G 7/0509; A61G 7/051; A61G 7/0512; A61G 13/0036; A61G 13/02; A61G 13/04; A61G 13/06; A61G 13/10; A61G 13/12; A61G 13/1285; A61G 13/129; A61G 13/00–13/08; A61H 1/00; A61H 1/001; A61H 1/005; A61H 1/0222; A61H 1/02; A61H 1/0218; A61H 1/0292; A61H 2001/0203; A61H 1/0296; A61H 1/0229; A61F 5/042; A61B 5/704; A61B 6/0407; A63B 22/0087; A63B 21/4029–21/4031; A63B 2023/006; A63B 23/0238
USPC ...... 602/32–36, 38–40; 601/1, 5, 23, 24, 26, 601/49, 33–35, 59; 5/18.1, 18.1 HS, 19, 5/20, 21, 47, 600, 607, 608, 610, 611, 5/612, 613, 614, 616, 617, 618, 619, 621
See application file for complete search history.

(56) References Cited

U.S. PATENT DOCUMENTS

| | | | | |
|---|---|---|---|---|
| 3,238,936 | A * | 3/1966 | Siedentop | A61F 7/007 5/284 |
| 3,289,674 | A | 12/1966 | Platt | |
| 4,243,025 | A * | 1/1981 | Jones | A61H 1/008 248/123.11 |
| 4,378,791 | A * | 4/1983 | Sarrell | A61H 1/0218 602/32 |
| 4,686,968 | A | 8/1987 | Scherger | |
| 4,732,141 | A | 3/1988 | Steffensmeier | |
| 5,052,378 | A | 10/1991 | Chitwood | |
| 5,094,228 | A | 5/1992 | Reinert | |
| 5,171,317 | A | 12/1992 | Corcoran | |
| 5,192,305 | A | 3/1993 | Sastre | |
| 5,192,306 | A | 3/1993 | Scott | |
| 6,152,950 | A | 11/2000 | Shealy | |
| 6,638,299 | B2 * | 10/2003 | Cox | A61G 13/009 5/617 |
| 6,788,968 | B2 | 9/2004 | Pettibon | |
| 6,821,288 | B2 * | 11/2004 | Schaeffer | A61H 1/0292 128/845 |
| 7,234,180 | B2 | 6/2007 | Horton | |
| 7,530,960 | B2 * | 5/2009 | Cook | A61H 1/005 601/46 |
| 7,601,132 | B2 | 10/2009 | Nichols | |
| 8,020,228 | B2 * | 9/2011 | Rao | A61G 13/12 5/621 |
| 8,029,453 | B2 * | 10/2011 | Graham | A61F 5/3784 602/32 |
| 8,079,971 | B2 | 12/2011 | Becerra | |
| 8,257,285 | B2 * | 9/2012 | Cook | A61H 1/005 5/915 |
| 8,584,281 | B2 | 11/2013 | Diel | |
| 2004/0077982 | A1 | 4/2004 | Reinecke | |
| 2006/0047237 | A1 * | 3/2006 | Pruett | A61G 13/009 602/16 |
| 2006/0074366 | A1 * | 4/2006 | Ryan | A61F 5/04 602/32 |
| 2006/0224097 | A1 * | 10/2006 | Bass | A61H 1/0218 602/32 |
| 2008/0113853 | A1 | 5/2008 | Jang | |
| 2009/0226055 | A1 | 9/2009 | Dankowicz | |
| 2010/0211099 | A1 * | 8/2010 | Radermacher | A61G 13/009 606/245 |
| 2012/0239059 | A1 | 9/2012 | Jagger | |
| 2013/0079823 | A1 * | 3/2013 | Kao | A61H 1/0222 606/237 |
| 2013/0269110 | A1 * | 10/2013 | Ackerman | A61G 7/0526 5/621 |
| 2015/0231013 | A1 * | 8/2015 | Bernardoni | A61G 13/0036 128/845 |

FOREIGN PATENT DOCUMENTS

| | | |
|---|---|---|
| WO | WO 2013/054992 | 4/2013 |
| WO | WO 2013/141613 A1 | 9/2013 |

OTHER PUBLICATIONS

Air-Flex Flexion-Distraction—Brochure—Hill Laboratories Company—Since 1945.
Anatomotor roller massage and spinal traction—Brochure—Hill Laboratories Company.
Introduction to the Three-dimensional Scoliosis Treatment According to Schroth—Article reprinted from Physiotherapy, Nov. 1992, vol. 78, No. 11 p. 810-815—Treatment Report.
Berry Translations Brochure—Translations Tales Catalog.
Chiropractic BioPhysics, CBP, The Science of Spinal Health—Berry Translational Traction Table—Brochure.
Chattanooga Brochure—Montane Tables—DJO Global Brochure.
Galaxy McManis Mobil-Trac Decompression Therapy & Multi-Technique Table—Copyright 2014—Brochure.
Galaxy Ultimate Table (Elevation, Hylo, and Flexion-Distraction)—Copyright 2014—Brochure.
Naplesnews.com Handling the curve: An alternative method for scoliosis—Web article—Scripps Interactive Newspapers Group—2014 The E.W. Scripps Co.
The Anatomy of a Proven Performer—Brochure—The Cox Table—Haven Innovation.
Deed E. Harrison, DC "Postural Alignment & Health Disorders: A Scientific Connection?" American Journal of Clinical Chiropractic.

* cited by examiner

APPARATUS FOR APPLYING MULTI-DIMENSIONAL TRACTION TO THE SPINAL COLUMN

CROSS-REFERENCE

Not Applicable.

GOVERNMENT RIGHTS

Not Applicable.

REFERENCE TO CDS

Not Applicable.

TECHNICAL FIELD

The present innovation is in the technical field of multi-dimensional traction therapy for correcting abnormal spinal curves and, in particular, to improved methods and equipment for use in that field.

BACKGROUND

The human spine has a normal, healthy structure with certain curves that provides for proper balance and shock absorption. However, aging, disease and injury can affect the spinal structure causing debilitating pain and immobilization. For instance, Scoliosis is a disease that imparts an unhealthy curvature to the spine.

In describing the shape and structure of the spine, it is important to discuss a few anatomical terms. The transverse axis (also the X-Axis) extends from left to right. The longitudinal axis (also the Y-Axis) extends from the head to the feet. The sagittal axis (also the Z-Axis) extends anterior to posterior. A lateral traction force is exerted in the transverse (left-to-right) axis. A distraction force is exerted in the longitudinal (head-to-foot) axis. A sagittal force is exerted in the sagittal (front-to-back) axis.

The natural, healthy spinal structure includes curves in the sagittal plane—the spine curves from front to back to provide proper balance and shock absorption. When viewed from the side, the cervical and lumbar vertebrae form healthy lordotic (concave toward the back of the spine) curves and the thoracic vertebrae form a healthy kyphotic (convex toward the back of the spine) curve. With Scoliosis, the spine curves in an unhealthy manner on the transverse plane—from left to right. This curve compromises the spine's ability to provide balance and support the weight of the head and upper body.

Improper spine structure is generally treated with exercise, physical medicine or surgery. Physical medicine uses traction—the application of a force to the patient's body in one or more of the above-described axes—to adjust the structure of the spine. Physical medicine can also be used to reshape the soft tissues—such as ligaments, tendons, and muscles—that support the spine in its unhealthy structure.

SUMMARY

Spinal structure treatment can be applied to a patient with a traction device that secures the patient to adjustable support portions and selectively imparts longitudinal Y-axis traction forces, (2) lateral X-axis traction forces and/or (3) sagittal Z-axis traction forces to the patient using a control system. In this way, precise, repeatable, and effective traction force treatment can be applied to the patient in multiple dimensions to adjust their spinal structure towards a normal, healthy structure.

Our traction device applies the traction forces through support portions. The support portions securely receive a portion of the patient's body, such as the head, chest, or pelvis. The support portions are adjustable, capable of being positioned longitudinally or rotated prior to the application of traction forces. The longitudinal positioning allows the traction device to receive and accommodate patients of varying heights. The longitudinal and rotational positioning of the support portions also allows the practitioner to target specific contact areas between the patient's body and the support portion. These specific contact areas allow the practitioner to treat patients with a variety of unhealthy spinal structures.

Our traction device uses a traction system that independently exerts a lateral force and a longitudinal force on the patient. In a patient with an unhealthy spinal structure, the ligaments of the back stretch and contract over time, yielding in an unhealthy manner to accommodate the unhealthy spinal structure. These ligaments connect between bones at a variety of angles. Our translation device can exert both a lateral traction force and a longitudinal traction force to act on ligaments that have yielded over time to the unhealthy spinal structure. The longitudinal traction (head-to-foot) force removes compressive forces on the spine, acts on longitudinally oriented ligaments that that have yielded over time to the unhealthy spinal structure, contributes to pain relief, and stretches longitudinally oriented soft tissues that have been adversely contracted or extended over time to support the spine in its unhealthy structure. The lateral traction (left to right) force stretches soft tissues that are aligned in the transverse (left to right) axis that have been adversely contracted or extended over time to support the spine in its unhealthy structure. By applying a combination of longitudinal traction forces, (2) lateral traction forces and/or (3) sagittal Z-axis traction forces, the traction device can effectively reshape both the spinal structure and the supporting soft tissues.

Our traction device allows the practitioner to selectively control the traction forces exerted by the traction system according to the prescribed treatment regimen. The control system controls each individual actuator of the traction system, allowing independent control of the lateral (X-Axis) and longitudinal (Y-Axis), and sagittal (Z-Axis) forces exerted through each support portion. The control system can allow the practitioner to set a maximum force for each traction force on the respective support portion. By setting maximum forces, a practitioner can establish a standardized treatment regimen designed to treat a specific unhealthy spinal structure. The control system can allow the practitioner to consistently use the standardized treatment regimen to exert predetermined traction force to the patient. This consistency allows for standardized treatment regimens that can be prescribed by the practitioner based on an individual diagnosis and then implemented by support staff.

The control system can optionally apply traction forces progressively over a predetermined period of time during the treatment period, in one or more axes. Such progressive increase maximizes the effectiveness of the treatment because of the viscoelastic nature of soft tissues. The progressive increase in force can have the cumulative effect of stretching or plastically deforming the soft tissues associated with the targeted treatment area such that the soft tissues are permanently reshaped even after the forces are removed. The progressive increase in force effectively reduces the muscle guarding and associated discomfort that is commonly encountered when a force is rapidly applied to a region of the body that involves one or multiple joints. The traction forces could be progressively increased within a single treatment, over a series of individual treatments, or both.

Our device also efficiently secures the patient to the support portions, thereby maximizing the effectiveness of the traction forces that are imparted to the support portions. Existing traction devices commonly use simple Velcro straps to secure the patient to the table. These simple straps often allow the patient to move relative to the traction device thereby compromising the effectiveness treatment. Our table can utilize securing elements, such as chains of rigid segmented links. These securing elements substantially limit the longitudinal movement of the patient relative to the respective support portion while the traction forces are applied. This increases the precision, repeatability, and effectiveness of the traction force treatment.

DESCRIPTION OF THE DRAWINGS

These and other features, aspects, and advantages of the present invention will become better understood with regard to the following description, appended claims, and accompanying drawings where:

DESCRIPTION

Figure 1:
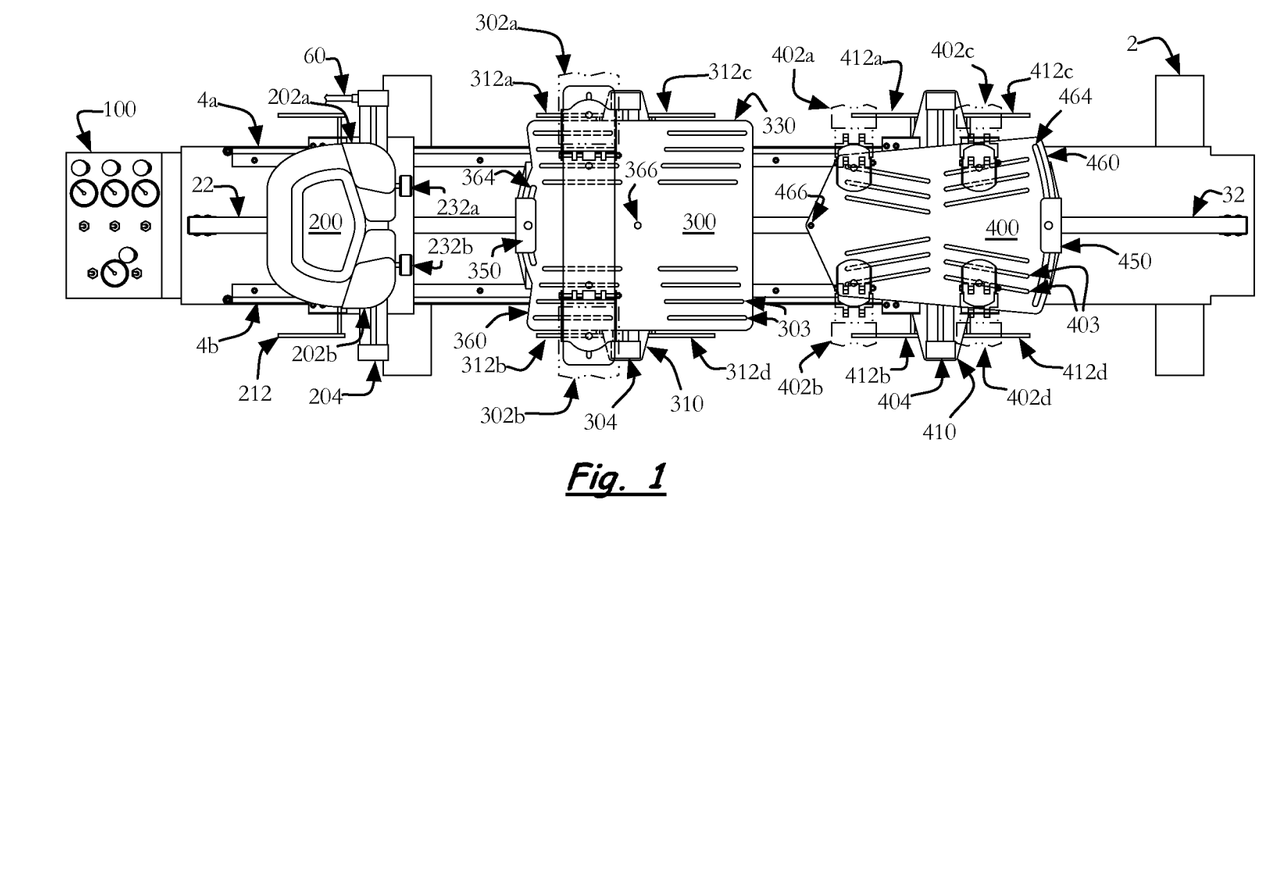
FIG. 1 depicts a top perspective view of the multi-dimensional traction table.

FIG. 1 shows a multi-dimensional traction table embodying the principles of the present innovation that is capable of providing precise, repeatable, and effective traction force treatment to a patient in multiple dimensions to adjust an unhealthy spinal structure towards a normal, healthy structure. Generally, the spinal structure treatment can be applied to a patient using the described traction device to secure the patient to the adjustable support portions and selectively impart a combination of longitudinal Y-axis traction forces, lateral X-axis traction forces and/or sagittal Z-axis traction forces to the patient using a control system in accordance with a prescribed treatment regimen.

The traction table applies the traction forces through support portions that securely receive a respective portion of the patient's body, such as the head, chest, or pelvis.

The support portions are adjustable, capable of being positioned longitudinally (in the Y-axis) prior to the application of traction forces. The longitudinal positioning allows the traction device to receive and accommodate patients of varying heights. The longitudinal positioning of the support portions also allows the practitioner to target specific contact areas between the patient's body and the support portion. These specific contact areas allow the practitioner to treat patients with a variety of unhealthy spinal structures.

The control system can allow the practitioner to set a precise, predetermined maximum force for each traction force on the respective support portion, including lateral, longitudinal and sagittal traction forces. By setting maximum forces, a practitioner can establish a standardized treatment regimen designed to treat a specific unhealthy spinal structure. The control system can allow the practitioner to consistently use the standardized treatment regimen to exert predetermined traction force to the patient. This consistency allows for standardized treatment regimens that can be prescribed by the practitioner based on an individual diagnosis and then implemented by support staff.

A head support portion 200 is configured to receive and restrain the patient's head. In a preferred embodiment, the head support portion corresponds to the size of an average adult head. The head support comprises a cushion upon which the patient's head rests. A pair of occipital restraints 202a, b is preferably provided on the head support portion whereby the patient's head can be selectively restrained. In the illustrated embodiment, the occipital restraints 202a, b protrude from the surface of the head support portion in a generally V-shape to receive the patient's neck while restraining the head.

A thoracic support portion 300 is configured to receive and restrain the patient's thoracic region. In a preferred embodiment, the size of the thorax support portion corresponds to the width and length of an average adult thorax. In a preferred embodiment, one or more securing elements 302a, b are provided and affixed to opposing lateral sides of the thoracic support portions.

A pelvic support portion 400 is configured to receive and restrain the patient's pelvic region. In a preferred embodiment, the width of the pelvic support portion corresponds to the width of an average adult pelvis and the length allows the pelvic support portion to engage both the pelvis and a portion of the thighs. In a preferred embodiment, one or more securing elements 402a, b, c, d are provided and affixed to opposing lateral sides of the pelvic support portions.

The patient can be secured to a respective support portions using a securing element 302, 402, such as a strap, so that the patient does not move relative to the support portion. In one embodiment, the securing elements 302, 402 have complementary pile and loop fastening material on an opposite side of the support portion to the point at which the strap is attached to the support portion. In a preferred embodiment, these securing elements 302, 402 are comprised of a semi-rigid chain or series of segmented links. The segmented links are a rigid material. The links are attached together into a chain or series that allows the segmented links to pivot relative to one-another where the links are joined together at a hinge. The hinge allows pivoting motion that allows the semi-rigid strap to flexibly curve inwardly toward the patient and outwardly away from the patient, while resisting movement in the longitudinal axis. It is also contemplated that the securing elements can be made up of both semi-rigid portions and flexible strap portions, where semi-rigid portions are attached to opposing sides of a respective support portion and the strap portion has a pile and loop fastening material for joining the two semi-rigid portions together around the patient. It is also contemplated that the two semi-rigid portions can be joined by a buckle or other known elements for securing two semi-rigid securing elements.

These semi-rigid securing elements limit the longitudinal movement of the patient relative to the respective support portion while the traction forces are applied. Existing traction devices generally use flexible straps to secure the patient to the table. Even when firmly tightened, these simple straps can allow the patient to move relative to the traction device thereby compromising the effectiveness of the treatment and producing discomfort or even injury to the patient. By properly yet safely securing the patient to the support portions, the semi-rigid securing elements allows this device to transfer the full effect of the traction forces that are imparted to the support portions. This increases the precision, repeatable, comfort and effectiveness of the traction force treatment.

The strap 302, 402 for the respective support portion can be selectively attachable to the support portions using a bracket 306a, 306b, 406a, 406b at an end of the respective strap. These brackets 306, 406 can be adjustably attached to the respective support portion in order to accommodate patients of varying sizes. The adjustable attachment is accomplished by mounting the brackets 306, 406 through a respective strap adjustment slot 303, 403. In a preferred embodiment, securing elements 302, 402 are provided and affixed to opposing lateral sides of the support portions 300, 400. These securing elements 302, 402 can be selectively attachable to the support portions 300,400 with a bracket 306, 406 at their respective ends. These brackets 306, 406 are adjustably attached to support portions 300, 400 through the securing element adjustment slots 303, 403 in order to accommodate patients of varying sizes.

Figure 2:
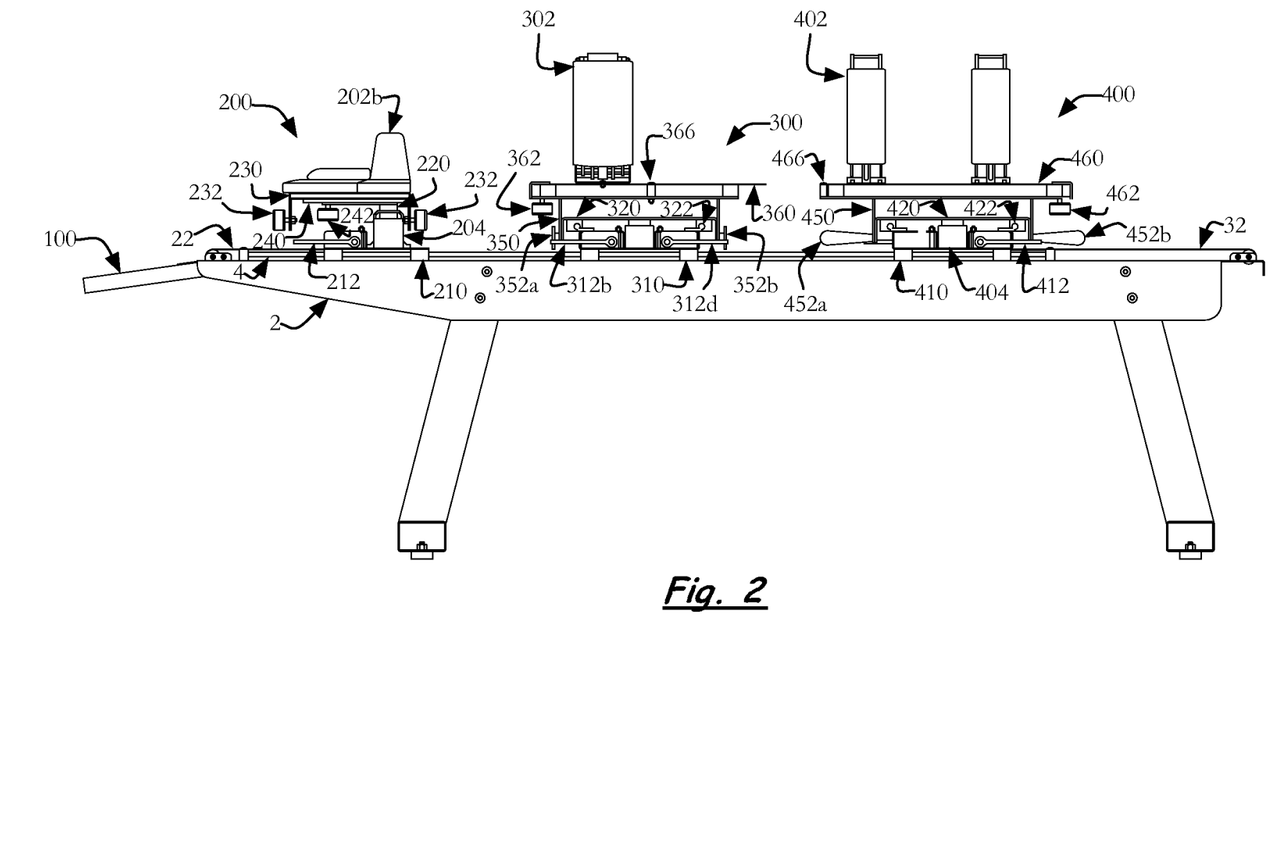
FIG. 2 depicts a side perspective view of the multi-dimensional traction table.
Figure 5:
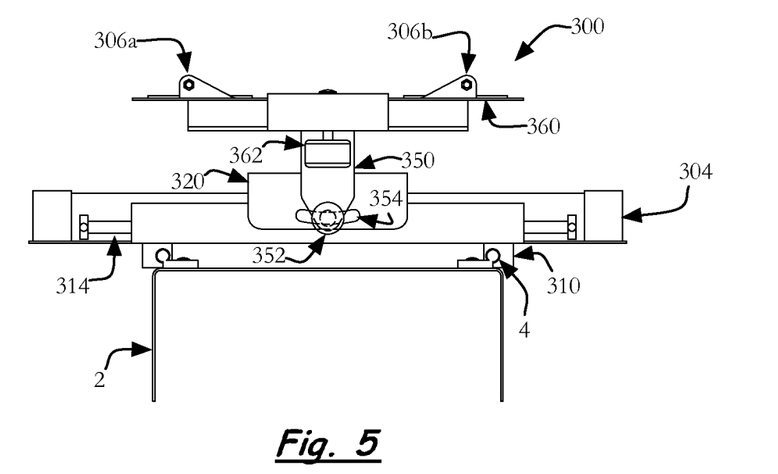
FIG. 5 depicts a side perspective view of the pelvic support portion.
Figure 8:
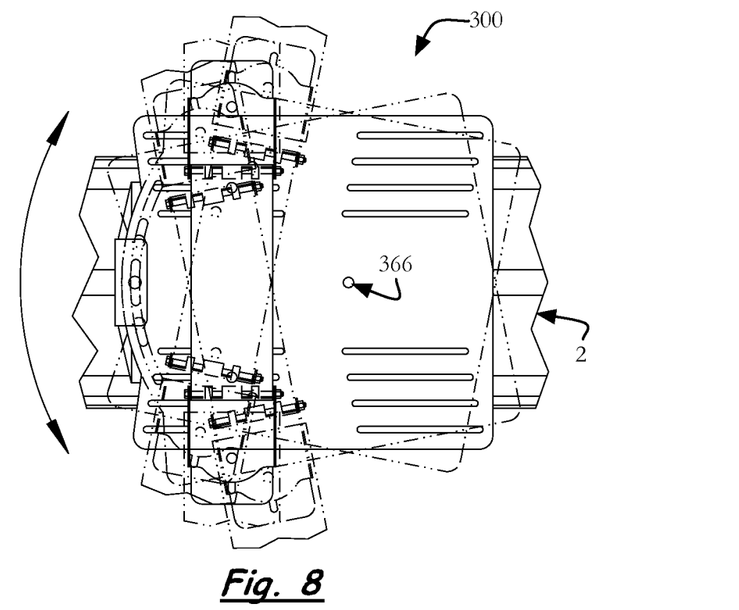
FIG. 8 depicts the rotational adjustment of the pelvic support portion.
Figure 9:
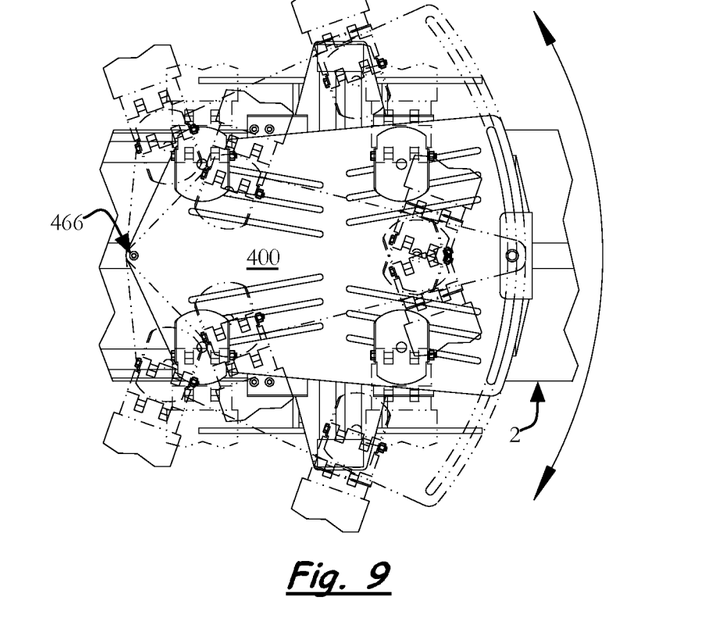
FIG. 9 depicts the rotational adjustment of the thoracic support portion.

FIGS. 8 and 9 show an embodiment of the pivoting adjustment mechanism that allows the respective support portion 200, 300, 400 to be selectively pivotally adjustable. The pivoting range of the thoracic support portion 300 about the sagittal axis is shown in FIG. 8. The pivoting adjustment mechanism of the thoracic support portion is illustrated in FIGS. 1, 2, and 5. The pivoting range of the pelvic support portion 400 about the sagittal axis is shown in FIG. 9. In a preferred embodiment, each of the support portions is capable of pivoting about the longitudinal axis and the sagittal axis of the body. The support portions 200, 300, 400 are, capable of being pivoted prior to the application of traction forces. The pivoting adjustment allows the support portions to rotate about a specific axis.

The support portions 200, 300, 400 are respectively comprised of one or more subframes. The various subframes allow for positioning, rotation, and movement in and about a variety of axes. As illustrated in FIG. 2, each respective support portion 200, 300, 400 is comprised of a longitudinal movement subframe 210, 310, 410 that is slidably mounted to a pair of longitudinal rails 4a, 4b that are mounted to the frame 2. A lateral movement subframe 220, 320, 420 is slidably mounted to a lateral actuator 204, 304, 404 respective longitudinal movement subframe 210, 310, 410. The respective pivot subframes are mounted to the lateral movement subframe 220, 320, 420.

Figure 4:
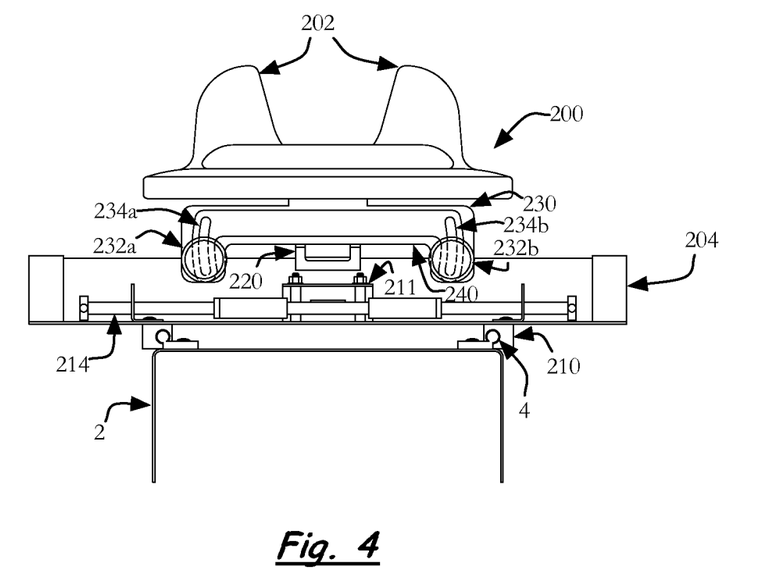
FIG. 4 depicts a side perspective view of the head support portion.

The cervical support portion 200 is comprised of several subframes to facilitate the pivotal range as well as the longitudinal and lateral motion. A cervical longitudinal subframe 210 is slidably mounted to the pair of longitudinal rails 4a, 4b. The longitudinal rails 4a, 4b are disposed parallel to each other and extend the length of the frame 2. Referring now to FIGS. 1, 2, and 4, the cervical longitudinal subframe 210 receives the pair of longitudinal rails 4a, 4b. The cervical longitudinal subframe 210 has a longitudinal position locking mechanism 211, which is shown in greater detail in FIGS. 13 and 14, and which is descried in greater detail below. Briefly, a cervical longitudinal position lock lever 212 is operably connected to the longitudinal position lock 213 to selectively engage or disengage a first longitudinal belt 22. As described in greater detail below, the first longitudinal belt 22 is operably connected to a first longitudinal traction actuator 20 in order to provide longitudinal traction to the patient through a respective support portion.

Figure 7:
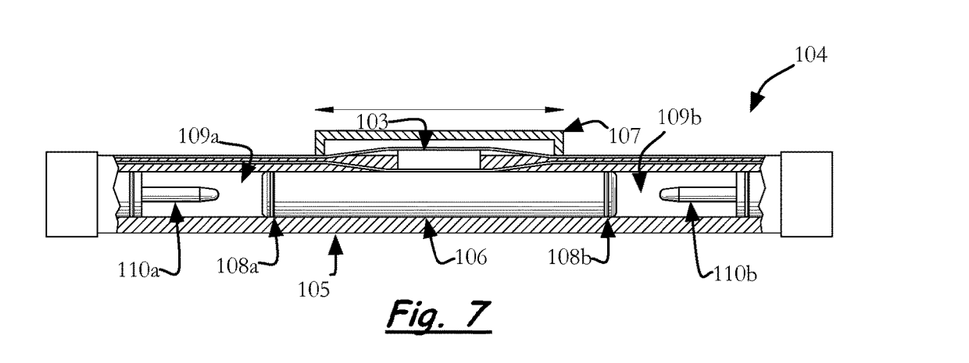
FIG. 7 depicts a cutaway view of the lateral actuator.
Figure 10:
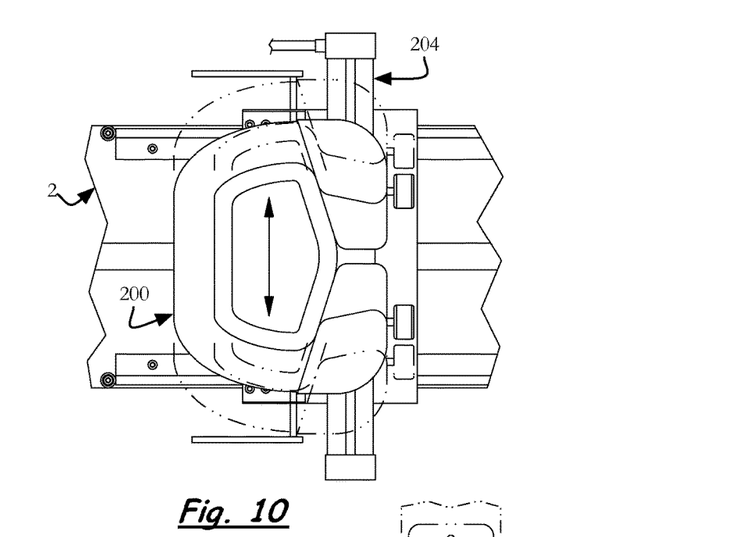
FIG. 10 depicts the lateral adjustment of the head support portion.
Figure 11:
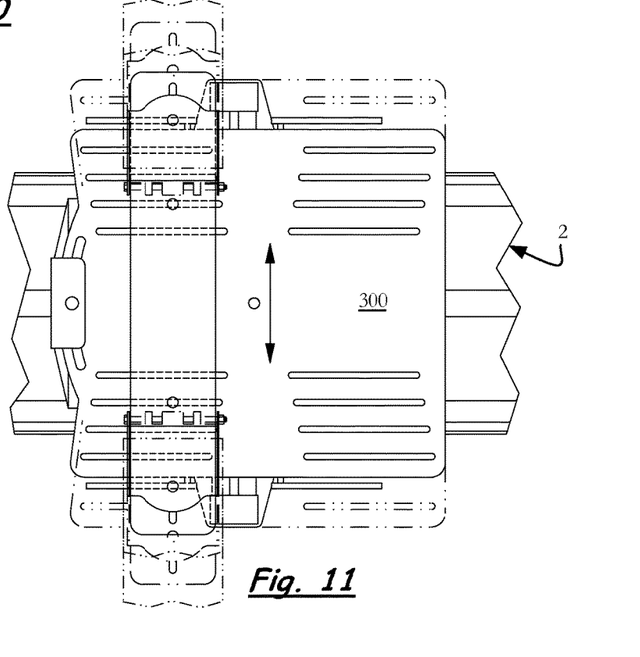
FIG. 11 depicts the lateral adjustment of the thoracic support portion.

The cervical support portion 300 is also capable of lateral motion in the transverse axis to provide the patient with lateral traction force. In order to facilitate this lateral motion, the cervical support portion 200 is comprised of a cervical lateral movement subframe 220. A cervical lateral actuator 204 is mounted to the cervical longitudinal subframe 210 and is operably connected to the cervical lateral movement subframe 220 to cause the cervical support portion 200 to move in the transverse axis, which is depicted in FIG. 10. Preferably, the cervical lateral actuator 204 is a rodless pneumatic actuator (as shown in FIG. 7) that is capable of imparting a lateral traction force on the cervical support portion 200 in the transverse axis. This force causes the thoracic support portion 200 to slide laterally relative to the frame 2. Relative to the longitudinal center of the frame, the lateral traction force can be generated toward the right or the left of the central axis according to the practitioner's prescribed treatment regimen.

The cervical support portion 200 is also capable of being selectively pivoted about the longitudinal axis and the transverse axis. In order to facilitate this pivotal adjustment, the cervical support portion 200 is comprised of a cervical longitudinal-transverse pivot subframe 230 that is pivotally mounted to the cervical lateral movement subframe 210. Referring to FIGS. 1, 2 and 4, a pair of cervical longitudinal-transverse pivot fasteners 232a, b are received by both the lateral movement subframe 210 and a respective cervical longitudinal-transverse pivot adjustment slot 234 in the cervical longitudinal-transverse subframe 230. When one or more of the cervical longitudinal-transverse pivot fasteners 232a, b are loosened, the cervical support portion 200 is capable of being pivoted about longitudinal axis and the transverse axis. The one or more cervical longitudinal-transverse pivot fastener 232a, b that have been loosened are capable of movement within the respective cervical longitudinal-transverse pivot adjustment slot 234a, b. Adjusting the pivot fasteners 232a, b relative to the right/left adjustment slots 234 will pivot the cervical longitudinal-transverse pivot subframe 230 about the longitudinal axis. Adjusting the pivot fasteners 232a, b relative to the top/bottom adjustment slots 234a, b will pivot the cervical longitudinal-transverse pivot subframe 230 about the transverse axis. When the cervical support portion 200 is pivoted to the desired position, the cervical longitudinal-transverse pivot fastener is tightened to secure the cervical support portion from further pivoting about the longitudinal axis or the transverse axis.

The cervical support portion 200 is also capable of being selectively pivoted about the sagittal axis. In order to facilitate this pivotal adjustment, the cervical support portion 200 is comprised of a cervical sagittal pivot subframe 240 that is pivotally mounted to cervical longitudinal-transverse pivotal subframe 230. Referring to FIGS. 2 and 4, a cervical sagittal pivot fastener 242 is received by both the cervical sagittal pivot subframe 240 and a cervical sagittal pivot adjustment slot (not shown) in the cervical longitudinal-transverse pivotal subframe 230. The cervical sagittal pivot adjustment slot is an elongated and arcuate shaped aperture in the cervical sagittal pivot subframe 240. When the cervical sagittal pivot fastener 242 is loosened, the cervical support portion 200 is capable of being pivoted about the sagittal axis. When the cervical support portion 200 is pivoted to the desired position, the cervical sagittal pivot fastener is tightened to secure the cervical support portion from further pivoting about the sagittal axis. The pivotal adjustment of the support portions also allows the practitioner to target specific contact areas between the patient's body and the support portion. These specific contact areas allow the practitioner to treat patients with a variety of unhealthy spinal structures.

The thoracic support portion 300 is also comprised of several subframes to facilitate the pivotal movement as well as the longitudinal and lateral traction forces. The thoracic support portion 300 is capable of longitudinal motion in the longitudinal axis. In order to facilitate this longitudinal motion, a thoracic longitudinal subframe 310 is slidably mounted to the frame 2. Referring to FIGS. 1, 2 and 5, the thoracic longitudinal subframe 310 is slidably mounted to the pair of longitudinal rails 4a, 4b. The thoracic longitudinal subframe 310 receives the pair of longitudinal rails 4a, 4b in order to guide the longitudinal traction force in the longitudinal axis. The thoracic longitudinal subframe 310 has two longitudinal position locking mechanisms 311a and 311b, which are shown in greater detail in FIGS. 13 and 14, which is described in greater detail below. Briefly, a first thoracic longitudinal position locking mechanism 311a has two thoracic longitudinal position lock levers 312a, 312b that are operably connected to a longitudinal position locking mechanism 311 to selectively engage or disengage the first longitudinal belt 22. A second thoracic longitudinal position locking mechanism 311b has two thoracic longitudinal position lock levers 312c, 312d that are operably connected to the longitudinal position lock 313 to selectively engage or disengage a second longitudinal belt 32. As described in greater detail below, the first longitudinal belt 22 is operably connected to the first longitudinal traction actuator 20 which provides longitudinal traction force toward the head-end of the frame. The second longitudinal belt 32 is operably connected to a second longitudinal traction actuator 30 in order to provide longitudinal traction force toward the foot-end of the frame.

The thoracic support portion 300 is also capable of lateral motion in the transverse axis. In order to facilitate this lateral motion, the thoracic support portion 300 is comprised of a thoracic lateral movement subframe 320. A thoracic lateral actuator 304 is mounted to the thoracic longitudinal subframe 310 and is operably connected to the thoracic lateral movement subframe 320 to cause the thoracic support portion 300 to move in the transverse axis, which is depicted in FIG. 10. Referring to FIGS. 2 and 5, the thoracic lateral movement subframe 320 receives a pair of thoracic lateral rails 322. The thoracic lateral rails 322 are mounted to the thoracic longitudinal subframe 310. The thoracic lateral rails 322 guide the thoracic lateral movement subframe 320. Preferably, the thoracic lateral actuator 304 is a rodless pneumatic actuator (as shown in FIG. 7) that is capable of imparting a lateral traction force on the thoracic support portion 300 in the transverse axis. This force causes the thoracic support portion 300 to slide along the thoracic lateral rails 322. Relative to the longitudinal center of the frame, the lateral traction force can be generated toward the right or the left of the central axis according to the practitioner's prescribed treatment regimen.

The thoracic support portion 300 is also capable of being selectively pivoted about the longitudinal axis. In order to facilitate this pivotal adjustment, the thoracic support portion 300 is comprised of a thoracic longitudinal pivot subframe 350 that is pivotally mounted to the thoracic lateral movement subframe 310. Referring now to FIGS. 1, 2, and 5, a thoracic longitudinal pivot fastener 352a, b is received by both the lateral movement subframe 310 and a thoracic longitudinal pivot adjustment slot 354 in the thoracic longitudinal subframe 350. The thoracic longitudinal slot 354 is an elongated and arcuate shaped aperture in the thoracic longitudinal subframe 350. When the thoracic longitudinal pivot fastener 352a, b is loosened, the thoracic support portion 300 is capable of being pivoted about the longitudinal axis. When the thoracic support portion 300 is pivoted to the desired position, the thoracic longitudinal pivot fastener is tightened to secure the thoracic support portion from further pivoting about the longitudinal axis.

The thoracic support portion 300 is also capable of being selectively pivoted about the sagittal axis. In order to facilitate this pivotal adjustment, the thoracic support portion 300 is comprised of a thoracic sagittal pivot subframe 360 that is pivotally mounted to thoracic longitudinal-transverse pivotal subframe 330. Referring to FIGS. 1, 2 and 5, a thoracic sagittal pivot fastener 362 is received by both the thoracic sagittal pivot subframe 360 and a thoracic sagittal pivot adjustment slot 364 in the thoracic longitudinal-transverse pivotal subframe 330. The thoracic sagittal pivot adjustment slot 364 is an elongated and arcuate shaped aperture in the thoracic longitudinal transverse pivotal subframe 330. When the thoracic sagittal pivot fastener 362 is loosened, the thoracic support portion 300 is capable of being pivoted about the sagittal axis at pivot point 366. When the thoracic support portion 300 is pivoted to the desired position, the thoracic sagittal pivot fastener is tightened to secure the thoracic support portion from further pivoting about the sagittal axis. The pivotal adjustment of the support portions also allows the practitioner to target specific contact areas between the patient's body and the support portion. These specific contact areas allow the practitioner to treat patients with a variety of unhealthy spinal structures.

Figure 6:
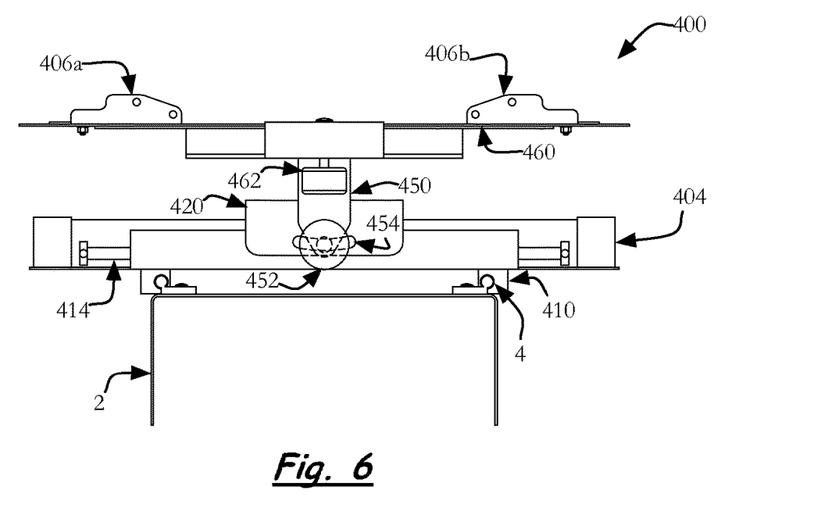
FIG. 6 depicts a side perspective detail view of the thoracic support portion.

The pelvic support portion 400 is comprised of several subframes to facilitate the pivotal range as well as the longitudinal and lateral motion. The pelvic support portion 400 is capable of longitudinal motion in the longitudinal axis. In order to facilitate this longitudinal motion, a pelvic longitudinal subframe 410 is slidably mounted to the frame 2. Referring to FIGS. 1, 2 and 6, the pelvic longitudinal subframe 410 is slidably mounted to the pair of longitudinal rails 4a, 4b. The pelvic longitudinal subframe 410 receives the pair of longitudinal rails 4a, 4b in order to guide the longitudinal traction force in the longitudinal axis. The pelvic longitudinal subframe 410 has a longitudinal position locking mechanism 411, which is shown in greater detail in FIGS. 13 and 14. Briefly, the pelvic longitudinal position locking mechanism 411 has two pelvic longitudinal position lock levers 412a, 412b that are operably connected to a longitudinal position lock 413 to selectively engage or disengage the second longitudinal belt 32. As described in greater detail below, the second longitudinal belt 32 is operably connected to the second longitudinal traction actuator 30 which provides longitudinal traction force toward the foot-end of the frame 2.

Figure 12:
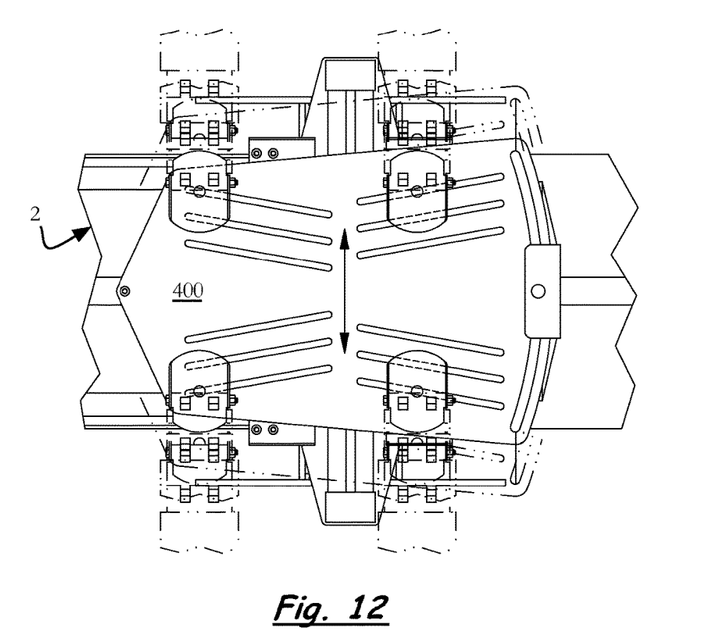
FIG. 12 depicts the lateral adjustment of the pelvic support portion.

The pelvic support portion 400 is also capable of lateral motion in the transverse axis. In order to facilitate this lateral motion, the pelvic support portion 400 is comprised of a pelvic lateral movement subframe 420. A pelvic lateral actuator 404 is mounted to the pelvic longitudinal subframe 410 and is operably connected to the pelvic lateral movement subframe 420 to cause the pelvic support portion 400 to move in the transverse axis, which is depicted in FIG. 12. Referring to FIGS. 2 and 6, the pelvic lateral movement subframe 420 receives a pair of pelvic lateral rails 422. The pelvic lateral rails 422 are mounted to the pelvic longitudinal subframe 410. The pelvic lateral rails 422 guide the pelvic lateral movement subframe 420. Preferably, the pelvic lateral actuator 404 is a rodless pneumatic actuator (as shown in FIG. 7) that is capable of imparting a lateral traction force on the pelvic support portion 400 in the transverse axis. This force causes the pelvic support portion 400 to slide along the pelvic lateral rails 422. Relative to the longitudinal center of the frame, the lateral traction force can be generated toward the right or the left of the central axis according to the practitioner's prescribed treatment regimen.

The pelvic support portion 400 is also capable of being selectively pivoted about the longitudinal axis. In order to facilitate this pivotal adjustment, the pelvic support portion 400 is comprised of a pelvic longitudinal pivot subframe 450 that is pivotally mounted to the pelvic lateral movement subframe 410. Referring now to FIGS. 1, 2, and 6, a pelvic longitudinal pivot fastener 452a, b is received by both the lateral movement subframe 410 and a pelvic longitudinal pivot adjustment slot 454 in the pelvic longitudinal pivot subframe 450. The pelvic longitudinal pivot adjustment slot 454 is an elongated and arcuate shaped aperture in the pelvic longitudinal pivot subframe 450. When the pelvic longitudinal pivot fastener 452a, b is loosened, the pelvic support portion 400 is capable of being pivoted about the longitudinal axis. When the pelvic support portion 400 is pivoted to the desired position, the pelvic longitudinal pivot fastener is tightened to secure the pelvic support portion from further pivoting about the longitudinal axis.

The pelvic support portion 400 is also capable of being selectively pivoted about the sagittal axis. In order to facilitate this pivotal adjustment, the pelvic support portion 400 is comprised of a pelvic sagittal pivot subframe 460 that is pivotally mounted to pelvic longitudinal/transverse pivotal subframe 450. Referring to FIGS. 1, 2 and 5, a pelvic sagittal pivot fastener 462 is received by both the pelvic longitudinal pivot subframe 450 and a pelvic sagittal pivot adjustment slot 464 in the pelvic sagittal pivot subframe 460. The pelvic sagittal pivot adjustment slot 464 is an elongated and arcuate shaped aperture in the pelvic longitudinal pivot subframe 450. When the pelvic sagittal pivot fastener 462 is loosened, the pelvic support portion 400 is capable of being pivoted about the sagittal axis at pivot point 466. When the pelvic support portion 400 is pivoted to the desired position, the pelvic sagittal pivot fastener 462 is tightened to secure the pelvic support portion from further pivoting about the sagittal axis. The pivotal adjustment of the support portions also allows the practitioner to target specific contact areas between the patient's body and the support portion. These specific contact areas allow the practitioner to treat patients with a variety of unhealthy spinal structures.

Another aspect of the multi-dimension traction device is that it applies a combination of longitudinal traction forces, lateral traction forces and/or sagittal Z-axis traction forces through a traction system. In this way, the traction device can effectively reshape both the spinal structure and the supporting soft tissues. The traction system comprises respective actuators to impart the combination of longitudinal traction forces, lateral traction forces and/or sagittal Z-axis traction forces onto the support portions. The actuators push or pull the support portions—and the respective portion of the patient's body—thereby effectuating the prescribed treatment regimen.

The multi-dimensional traction device uses a traction system that exerts a lateral force and a longitudinal force on the patient. In a patient with an unhealthy spinal structure, the ligaments of the back stretch and contract to accommodate the unhealthy spinal structure. These ligaments connect between bones at a variety of angles. The multi-dimensional translation device can exert both a lateral force and a traction force to act on ligaments that support the unhealthy spinal structure. The longitudinal traction (head-to-foot) force removes compressive forces on the spine, acts on longitudinally oriented ligaments that reinforce the unhealthy spinal structure, contributes to pain relief, and stretches longitudinally oriented soft tissues that have been contracted or extended over time to support the spine in its unhealthy structure. The lateral traction (left to right) force stretches soft tissues that are aligned in the transverse (left to right) axis that have been contracted or extended over time to support the spine in its unhealthy structure.

In order to impart longitudinal traction forces, the support portions 200, 300, 400 are selectively moveable—relative to the frame 2—in the longitudinal axis. The longitudinal force is imparted with one or more longitudinal actuators 20, 30. The longitudinal actuators 20, 30 are operably connected to one or more of the support portions.

Figure 3:
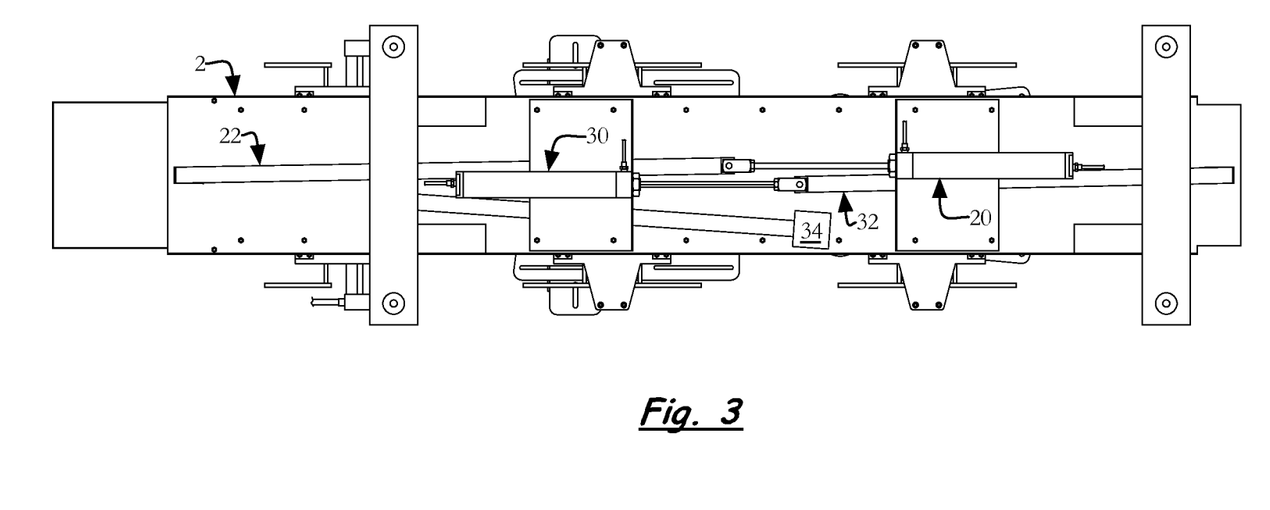
FIG. 3 depicts a bottom perspective view of the multi-dimensional traction table.

The longitudinal actuators 20, 30 generate the longitudinal traction forces. The illustrated embodiment is capable of generating longitudinal traction forces in both directions in the longitudinal axis—a first longitudinal traction force toward the head-end of the frame 2 and a second longitudinal traction force toward the foot-end of the frame 2. Referring now to FIG. 3, the first longitudinal actuator 20 and the second longitudinal actuator 30 are shown mounted to the bottom of the frame 2. The first longitudinal actuator 20 is configured to pull a first longitudinal strap 22 out of a first strap tensioner (not shown) that is located on the bottom surface of the device. The first longitudinal strap 22 passes through a slot in the frame and engages a first strap roller 26. The direction of the movement of the strap 22 is reversed after passing through the slot. The strap travels from the first strap tensioner, longitudinally along the center of the top of the frame 2, over the first strap roller 26, and then to the underside of the frame 2 where the strap is attached to the first longitudinal actuator 20. As the first longitudinal actuator retracts, the first strap 22 is pulled out of the first strap tensioner. The first strap tensioner maintains the first strap 22 under slight tension and could comprise a spring-driven tensioner. As the first longitudinal actuator extends, the first strap 22 is automatically taken up and stored within the tensioner as the actuator tension is released. The second longitudinal actuator 30 is configured to pull a second longitudinal strap 32 in the opposite direction of the first longitudinal strap 22 out of a second strap tensioner 34. The second longitudinal strap 32 is attached to the second longitudinal actuator 30 at the underside of the frame 2, the strap continues longitudinally toward the foot-end of the frame, travels through a slot, is received by a second strap roller 36 near the foot-end of the frame. After passing through the slot, the direction of the second longitudinal strap 32 is reversed, where it continues longitudinally toward the head-end of the frame 2. The second longitudinal strap 32 passes through another slot in the frame 2 and is received by another roller (not shown) and again reverses direction toward the foot-end of the frame 2 where the strap is received and stored in the second strap tensioner 34. In summary, the first longitudinal strap 22 is pulled toward the head-end and the second longitudinal strap 32 is pulled toward the foot-end of the frame 2—on the top surface of the frame. Individual tensioners maintain the tension on each strap independently. For example, the tensioner could comprise a spring, actuator or other biasing member.

Figure 13:
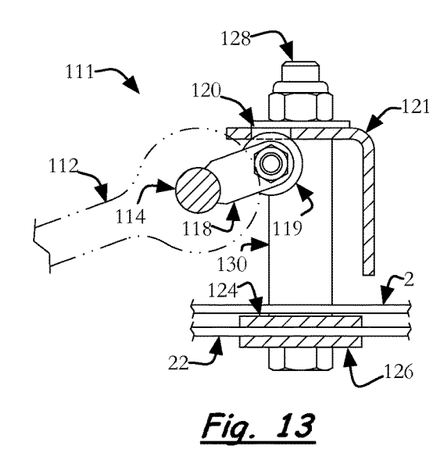
FIG. 13 depicts the longitudinal position locking mechanism in an engaged state.
Figure 14:
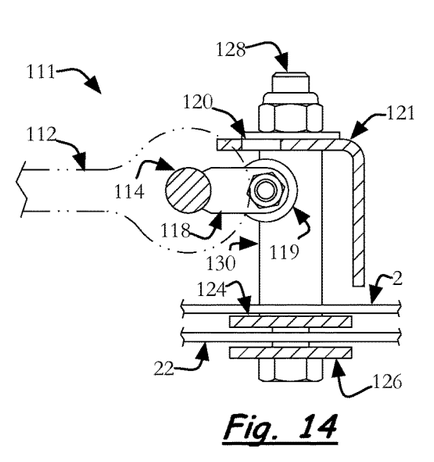
FIG. 14 depicts the longitudinal position locking mechanism in a disengaged state.

The practitioner can use the multi-dimensional traction table to selectively impart a longitudinal traction force onto the patient in accordance with the prescribed treatment regimen. Each support portions 200, 300, 400 also comprises a respective longitudinal position locking mechanism 211, 311, 411. The longitudinal position locking mechanisms 211 (shown in FIG. 4), 311 (not shown, located under thoracic support portion 300), 411 (not shown, located under pelvic support portion 400) can operably connect one or more support portions 200, 300, 400 to one of the longitudinal traction straps 22, 32. When the longitudinal position locking mechanism 211, 311, 411 is in the engaged state, the support portion travels with the longitudinal traction strap 22, 32. Referring now to FIGS. 13 and 14, a generic longitudinal position lock 111 is shown in detail as an embodiment of the cervical longitudinal position locking mechanism 211, thoracic longitudinal position locking mechanism 311, and pelvic longitudinal position locking mechanism 411. The longitudinal position locking mechanism comprises a lever 112 for engaging a top lock plate 124 and a bottom lock plate 126. A lock bolt 128 extends through the entire locking mechanism operably connect the top lock plate 124 and the bottom lock plate 126 with the engagement plate 121. The lock bolt 128 passes through a lock bolt sheath 130 to maintain the proper vertical position of the lock bolt when unlocked. When the top lock plate 124 and bottom lock plate 126 are engaged, they compress the longitudinal traction strap 22, 32 that is disposed between the plates 124, 126. In order to lock the lower longitudinal traction strap without affecting the upper longitudinal traction strap, a pair of washers (not shown) can be mounted above the top lock plate 124. The washers lower the locking mechanism to engage the lower traction strap while providing a passage for the upper traction strap to pass through unaffected by the engage/unengaged status of the locking mechanism.

In order to provide the practitioner easy access to the longitudinal position locking mechanism 111, the lever 112 is disposed on the lateral sides of the respective support portion 200, 300, 400. The lever 112, 212, 312 is connected to a longitudinal position rod 114, 214, 314. Rotation of the longitudinal position rod 114, 214, 314 turns a cam 118 that is mounted to the rod 114. The lever 212, 312, 412 cooperates with the cam 118 for selectively engaging or disengaging the lock 111 with a respective longitudinal belt 22, 32. The cam 118 pushes up on the lock bracket 122.

In the locking mechanism's disengaged state, the support portion is adjustably positionable in the longitudinal axis relative to both the frame 2 and the respective longitudinal belt 22, 32. In the locking mechanism's engaged state, the support portion 200, 300, 400 is immovable relative to the respective longitudinal belt 22, 32 but remains moveable relative to the frame 2. It is important to emphasize that the longitudinal locking mechanism 211, 311, 411 allows the support portions to be selectively adjusted to a predetermined zero position along the longitudinal axis based on the height of the patient in order to accommodate patients of varying heights. However, the support portions 200, 300, 400 remain capable of moving in the longitudinal axis relative to the frame 2 in cooperation with the respective longitudinal belt 22, 32 even when the locking mechanism is engaged. In this manner, the support portions 200, 300, 400 are capable of being selectively adjusted to a predetermined zero position along the longitudinal axis of the frame 2 and the multi-dimensional traction table is capable of imparting a longitudinal traction force from the predetermined zero position. The practitioner adjusts the support portion 200, 300, 400 to the predetermined zero position by selectively disengaging the longitudinal position lock of a respective support portion and sliding the support portion along the longitudinal rails 4a, 4b to the predetermined longitudinal position corresponding with the patient's height.

The longitudinal position lock 111 is maintained in the engaged state by a cam roller 119 engaging a lock slot 120 in the lock bracket 122. When the lever 112 rotates the cam roller 119 into the engaged position, the cam roller is partially received by the lock slot 120, as shown in FIG. 13.

Optionally, the support portions 200, 300, 400 can impart opposing longitudinal traction forces onto the patient. Referring now to FIG. 2, the cervical support portion 200 is capable of longitudinal movement toward the head-end of the frame 2 and the pelvic support portion 400 is capable of longitudinal movement toward the foot-end of the frame 2. The thoracic support portion 300 is capable of longitudinal movement either toward the head-end or the foot-end of the frame 2. The practitioner selectively engages either the first thoracic longitudinal lever 312 to engage the first longitudinal strap 22 or the practitioner engages the second thoracic longitudinal lever 316 to engage the second longitudinal strap. Alternatively, one or more support portions 200, 300, 400 can be longitudinally fixed relative to frame 2 and one or more support portions 200, 300, 400 can be selectively connected to the longitudinal strap 22, 32.

Taken together, the longitudinal traction actuator 20, 30, the longitudinal belt 22, 32, and the longitudinal belt tensioner 34 comprise a longitudinal drive system. Alternatively, the longitudinal belt 22, 32 could be a small roller chain or any number of other commercially available chain types. The longitudinal traction actuator 20, 30 could also be rotary in its engagement of the belt or chain. It is also contemplated that the longitudinal drive system could comprise an actuator directly connected to the support portions 200, 300, 400, for example the longitudinal traction actuator 20, 30 could be linear electro-mechanical, hydraulic or pneumatic that is directly connected to a respective support portion.

The traction system is also capable of imparting lateral forces on one or more support portions 200, 300, 400. The traction system comprises respective actuators mounted to the longitudinal movement subframe 210, 310, 410 of the support portion 200, 300, 400. Referring to FIG. 7, the lateral drive system can comprise a rodless actuator 104. The rodless actuator 104 is known in the art, but generally the rodless actuator 104 has an elongated body 105 with a piston 106 that is movable within a hollow chamber within the body 105. The chamber is divided into two subchambers, a first subchamber 109a and a second subchamber 109b. A first valve 110a is disposed in the first subchamber 109a and a second valve 110*b* is disposed in the second subchamber 109*b*. The piston 106 has a first seal 108*a* and a second seal 108*b*, that constrains the fluid that enters the first chamber 109*a* from entering the second chamber 109*b*.

The lateral position of the individual support portions 200, 300, 400 start at the lateral center of the multi-dimensional traction device, and the lateral traction forces are applied from that central orientation. As described further below, the control system controls the activation and the force of the lateral actuator on the support portion 200, 300, 400. Referring again to the rodless actuator illustrated in FIG. 7, the ratio of the fluid pressure between the first chamber 109*a* and the second chamber 109*b* causes the movement of the piston 106. Upon the introduction of fluid pressure into one subchamber, the piston 106 will move towards the opposite end of the hollow chamber within the body 105. The piston 106 is magnetically linked to a carriage 103 that travels in synchrony with the piston. The support portions 200, 300, 400 receive the lateral traction force by being mounted to the lateral movement subframe 107—this generic illustrated lateral movement subframe 107 corresponds to the lateral movement subframe 220, 320, 420 on the respective support portions—that is mounted to the carriage 103. The lateral traction forces generated by the actuator are imparted through the support portion 200, 300, 400 to the patient, who is being securely held by the support portion.

The traction system comprises a plurality of actuators to generate the various traction forces. As used in this document, an actuator is a device that converts energy into physical movement. A variety of alternative actuators are contemplated, such as an electrical linear motor, electrical stepper motor, an electric solenoid, etc., and may act upon the support portion by either pulling or pushing. Alternatively, the actuator may be a piston that is pneumatic, fluidically, or hydraulically positioned to act upon an actuator. The energy source of the actuator can be operator-generated, mechanically-generated, electronically-generated, or programmatically generated and transmitted by any effective means, such as via cable, rope, strap, magnetic-induction, or other linear actuator or force transmitter. The actuator action can also be generated by fluid power, such as hydraulic, pneumatic, or other energizing force that is in communication with the conforming arm. Preferably, the traction forces are generated by a pneumatic actuator. A pneumatic or fluid source of a selected regulated pressure may actuate a single or multiple support portions 200, 300, 400. One or more respective supply lines 60 connects the pneumatic or fluid source with the respective actuator.

The traction system is also capable of concurrently imparting longitudinal Y-axis and lateral X-axis forces to one or more support portions. The net force that is applied the patient is the sum of the forces applied to the surface. For example, in an embodiment where the traction system applies both lateral X-axis force and longitudinal Y-axis force to the same support portion, then net force can be calculated as a force vector within the longitudinal-lateral plane of the patient.

The traction system is also capable of imparting sagittal Z-axis traction forces to the patient (not shown in the illustrated embodiment). It is contemplated that the traction system could incorporate one or more sagittal traction force actuators to apply sagittal traction force to the cervical region or the pelvic region of the patient, regions where the healthy spinal structure curves forward in the sagittal axis. The sagittal Z-axis traction forces can be imparted from above or below the patient. If situated above the patient, the sagittal traction force would pull on the patient. For example, a generally U-shaped yoke is positioned above the patient. The yoke supports an actuator that is operably coupled with a rope for exerting the sagittal traction force on the patient. The rope could also be a belt, cable, or chain. The rope can be connected to a releasable harness, which is placed around the patient. The actuator causes the rope to exert a sagittal traction force on the patient. During application of sagittal traction, the patient is secured in place at the thoracic and pelvic supports, which provides an opposite restraining allowing the sagittal traction force to slowly stretch the target soft tissues. Alternatively, the sagittal traction force can be applied from below the patient. In this embodiment, a sagittal traction force actuator is moved into proper longitudinal position. Activation of the sagittal actuator applies the sagittal traction forces to the patient directly.

The multi-dimensional traction device uses a control system 100 to control the traction forces imparted through the traction system. FIG. 1 shows one embodiment of the control system 100. In the illustrated embodiment, the control system 100 is an analog system that is preconfigured to independently control the various actuators of the traction system. The control system can be used to impart a maximum traction force in accordance with the prescribed regimen for each individual actuator. For instance, the control system may be a fluidic control device.

Alternatively, the traction forces imparted by the traction system can be controlled using a control system 100 that has an electronic controller that controls the actuators. The control system 100 could include electro-pneumatic control units that are interposed in the supply lines 60 between a source of pressurized gas and the air cylinders of the traction system. The control system 100 selectively commands a value to a respective one of the plurality of actuators that corresponds to the prescribed treatment regimen to achieve the selected traction force and regulates the admittance of pressurized air to the actuators of the traction system. To that end, the electronic embodiment of the control system 100 has a processor that accesses a computer-readable medium to perform operations by the actuators via one or more actuator interfaces/drivers of:
  a. responding to a user input on a user interface (UI) to impart a prescribed regimen of traction force to a patient by associating a desired maximum traction force with a dimension of movement of a respective support portion; and
  b. selectively actuating the appropriate support portion to impart the appropriate traction force onto the patient, wherein the selectively actuating creates a selected traction force of a selected one of the support portions.

To that end, the computer-readable medium may contain a support portion control application, a spinal-structure-to-support-portion mapping data structure, a traction force value determining calculator, a net force vector calculator, a temperature regulation application, and a traction force sensing utility.

A control system, controls the activation and power of the actuators. In one embodiment, the control system controls the activation of individual actuators. Each actuator controls movement of an individual support portion 200, 300, 400. Controlling individual actuators allows the control system to apply the prescribed treatment regimen to the patient. In another embodiment, a single actuator can control the movement of more than one support portion 200, 300, 400.

The control system 100 can optionally apply traction forces progressively over a predetermined period of time during the treatment period, in one or more axis. Such progressive increase maximizes the effectiveness of the treatment because of the elastic nature of soft tissues. The progressive increase in force can have the cumulative effect of stretching or plastically deforming the soft tissues associated with the targeted treatment area such that the soft tissues are permanently reshaped even after the forces are removed. The progressive increase in force also avoids exposing the patient to unacceptable levels of discomfort, which the patient would likely feel if the maximum force was applied at the beginning of the treatment. The traction forces could be progressively increased within a single treatment, over a series of individual treatments, or both.

The treatment parameters, including for example, peak longitudinal traction force for a respective support portion, peak lateral traction force for a respective support portion, rate of increase of traction force, and length of treatment time, will vary between patients and between treatments. Different patients have different needs, which means that the force and time values selected for different patients are likely to vary. Even with the same patient, it is contemplated that several different treatments will be involved over a period of several days or weeks, with each treatment typically being slightly different than the previous treatment.

The control system can also include one or more safety switches. The safety switches can instantly depressurize the actuators of the traction system. The safety switch would allow the practitioner or the patient to immediately override the control system 100 and stop the treatment, should the need arise.

Practitioners can use physical medicine to treat unhealthy spinal structures and the soft tissues that support that structure. Spinal structure treatment can be applied to a patient with a traction device that secures the patient to adjustable support portions and selectively imparts longitudinal and distraction forces to the patient using a control system. In this way, precise, repeatable, and effective traction force treatment can be applied to the patient in multiple dimensions to adjust their spinal structure towards a normal, healthy structure.

In another aspect, a temperature regulator may be connected to the support portions. In an exemplary aspect, the temperature regulator may be a fluid conduit connected to a source for temperature regulated fluid to affect a temperature of the patient by regulating a flow of the temperature regulated fluid through the plurality of support portions. Alternatively, the temperature regulator may be an electrical temperature regulator. In an exemplary aspect, the electronic controller may have a temperature control interface for controlling the temperature regulator.

Additionally, the support portions can impart a warming or cooling effect upon the patient by pumping temperature regulated fluid, such as heating or cooling fluids, within the support portions. Alternatively, resistive heating or piezoelectric heating/cooling may be implemented. The intimate contact of the support portions facilitates rapid heat transfer. The control system can monitor the temperature of the object and pump fluid for heating or cooling the object to maintain the desired temperature.

It should also be appreciated that while the multi-dimensional traction table is illustrated and generally described as a horizontal table, the principals would work equally well in a vertical, angled orientation, adjustable angle orientation, or tilt table. The angled orientation, adjustable angle orientation, or tilt table could include the capability of inversion positioning, where the patient's feet are positioned above their head. In a vertically oriented traction device, the patient would be secured to the respective support portions in a standing position. It is also contemplated that the device could be incorporated with a tilting feature, allowing the patient to approach the device while standing and the device tilts to a horizontal orientation.

Additionally, the multi-dimensional traction table could incorporate a vibration mechanism. Vibration mechanisms are well known in the industry and thus the vibration mechanism is not illustrated or described in detail. The vibration mechanism is coupled to one or more support portions in the usual manner.

In another embodiment, the support surfaces are mounted to a single longitudinal rail. The single longitudinal rail can be centrally mounted respective to the frame. The single longitudinal rail is keyed such that a non-rotating linear bearing is capable of longitudinally sliding on the single longitudinal rail. To that effect, the single longitudinal rail could have a square cross section or a circular cross section with a notch, groove, bump, bulge, or blip that corresponds to a corresponding keyed non-rotating linear bearing.

In the single longitudinal rail embodiment, a longitudinal pivot mount is is pivotally mounted to the non-rotating linear bearing to allow the support surface to pivot about the longitudinal axis. The longitudinal pivot mount could comprise a tensioned sleeve with a tensioner or a sleeve with a threaded hole to receive a corresponding fastener through the longitudinal pivot mount and securely fasten through to the single longitudinal rail.

In the single longitudinal rail embodiment, pivoting about the sagittal axis can be accomplished with a sagittal pivot subframe as described above can be mounted to the longitudinal pivot mount. Further, the lateral traction forces can be applied using a lateral movement subframe as described above.

Although the present innovation has been described in considerable detail with reference to certain preferred versions thereof, other versions are possible. Therefore, the spirit and scope of the appended claims should not be limited to the description of the preferred versions contained herein.

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

It should be appreciated that any patent, publication, or other disclosure material, in whole or in part, that is then to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is the to be incorporated by reference herein, but which conflicts with existing definitions, statements, or other disclosure material set forth herein, will only be incorporated to the extent that no conflict arises between that incorporated material and the existing disclosure material.

The invention claimed is:

1. A physical medicine table for treating a patient's spine comprising:

a. a frame having a longitudinal axis and a transverse axis;
a plurality of support portions that are configured to receive a patient, wherein the plurality of support portions are attached to the frame and selectively spaced apart along the longitudinal axis of the frame;
c. wherein a first support portion comprises:
   i. a first longitudinal movement subframe slidably mounted to the frame;
   ii. a first lateral movement subframe slidably mounted to the first longitudinal movement subframe and configured to move in the transverse axis;
   iii. a rotational adjustment subframe mounted to the first lateral movement subframe, the rotational adjustment subframe configured to selectively rotate;
d. a traction system comprising:
   i. a first lateral actuator centrally mounted to the first longitudinal movement subframe and centrally disposed under the rotational adjustment subframe;
   ii. wherein the traction system is configured to exert a first lateral force upon the first lateral movement subframe without rotating the first lateral movement subframe and without rotating the first support portion, wherein the first lateral force is perpendicular to the longitudinal axis of the frame, and the traction system is further configured to exert a longitudinal force upon at least one of the plurality of support portions; and
e. a control system that selectively controls the first lateral force and the longitudinal force exerted by the traction system.

2. The physical medicine table of claim 1, further comprising at least two securing elements, the at least two securing elements:
   a. mounted to the first support portion; and
   b. configured to secure a respective area of the patient's body against movement relative to the first support portion during lateral movement of the first lateral movement subframe.

3. The physical medicine table of claim 2, wherein the at least two securing elements are a chain of segmented links.

4. The physical medicine table of claim 1, wherein
   b. a second support portion comprising:
      ii. a second longitudinal movement subframe slidably mounted to the frame;
      iii. a second lateral movement subframe;
   c. the traction system comprises:
      iv. a longitudinal fluid-pressure-operated power device operably connected to the first support portion and the second support portion and configured to move the first support portion and the second support portion in the longitudinal axis; and
      v. a first lateral fluid-pressure operated power device operably connected to the first lateral movement subframe and oriented perpendicular to the longitudinal axis of the physical medicine table and configured to exert the first lateral force parallel to the transverse axis to bidirectionally move the first lateral movement subframe in the transverse axis relative to a central axis without rotating the first lateral movement subframe; and
      vi. a second lateral fluid-pressure operated power device operably connected to the second lateral movement subframe and oriented perpendicular to the longitudinal axis of the physical medicine table and configured to exert a second lateral force parallel to the transverse axis to bidirectionally move the second lateral movement subframe in the transverse axis relative to the central axis without rotating the second lateral movement subframe; and
   d. the control system is operably connected with the longitudinal fluid-pressure operated power device and the first lateral fluid-pressure operated power device and the second lateral fluid-pressure operated power device and adapted for connection with a source of pressurized fluid for supplying pressurized fluid to the longitudinal fluid-pressure operated power device and the first lateral fluid-pressure operated power device and the second lateral fluid-pressure operated power device in response to receiving a control signal.

5. The physical medicine table of claim 4, wherein the control system is capable of:
   a. receiving a preset longitudinal force limit and a preset lateral force limit;
   b. progressively increasing the longitudinal force exerted by the traction system over a predetermined period of time during a treatment period without exceeding the preset longitudinal force limit; and
   c. progressively increasing the first lateral force and the second lateral force exerted by the traction system over the predetermined period of time during the treatment period without exceeding the preset lateral force limit.

6. The physical medicine table of claim 5, wherein one of the plurality of fluid-pressure-operated power device is pneumatically operated.

7. The physical medicine table of claim 1, further comprising:
   a. a thoracic securing element mounted to a thoracic support portion and configured to exert a downward restraining sagittal force upon the patient;
   b. a pelvic securing element mounted to a pelvic support portion and configured to exert a downward restraining sagittal force upon the patient;
   c. a sagittal adjustment mechanism disposed between the thoracic support portion and the pelvic support portion, wherein the sagittal adjustment mechanism is configured to exert an opposing sagittal force upon the lumbar curve of the spine, wherein the opposing sagittal force is exerted in opposition to the restraining sagittal force exerted by the thoracic securing element and the pelvic securing element.

8. The physical medicine table of claim 1, further comprising:
   a. a first longitudinal rail mounted to the frame;
   b. wherein each of the plurality of support portions comprises a respective longitudinal movement subframe that is slidably mounted upon the first longitudinal rail; and
   c. wherein the traction system is configured to independently and concurrently impart both the first lateral force to the first lateral movement subframe and the longitudinal force to at least one of the longitudinal movement subframe.

9. The physical medicine table of claim 1, wherein the rotational adjustment subframe comprises an arcuate slot and is configured to selectively allow rotation of the rotational adjustment subframe about at least one of a sagittal axis of the physical medicine table and a longitudinal axis of the physical medicine table.

10. An apparatus for treating a patient's spine to change the shape thereof, the apparatus comprising:
   a. a frame having a longitudinal axis;
   a plurality of support portions spaced apart along the longitudinal axis wherein a first support portion comprises:

i. a first longitudinal movement subframe slidably mounted to the frame and configured to move in the longitudinal axis;
ii. a first lateral movement subframe slidably mounted to the first longitudinal movement subframe;
iii. a first pivot subframe mounted to the first lateral movement subframe, the first pivot subframe configured to rotate relative to the frame;
iv. a lateral actuator mounted to the first longitudinal movement subframe and the first lateral movement subframe, the lateral actuator configured to move the first lateral movement subframe to the right of and to the left of a central orientation in a transverse axis without rotating the first lateral movement subframe and without rotating the first support portion; and
f. a longitudinal adjustment mechanism for applying a distraction force to the first longitudinal movement subframe.

\* \* \* \* \*